United States Patent [19]

Young

[11] Patent Number: 4,894,373

[45] Date of Patent: Jan. 16, 1990

[54] ANTIESTROGENS AND THEIR USE IN TREATMENT OF MENOPAUSE AND OSTEOPOROSIS

[75] Inventor: Ronald L. Young, Houston, Tex.

[73] Assignee: BCM Technologies, Inc., Houston, Tex.

[21] Appl. No.: 143,081

[22] Filed: Jan. 12, 1988

Related U.S. Application Data

[63] Continuation-in-part of Ser. No. 660,510, Oct. 12, 1984, Pat. No. 4,729,999.

[51] Int. Cl.⁴ .............. A61K 31/535; A61K 31/445; A61K 31/40; A61K 31/19
[52] U.S. Cl. .................... 514/239.2; 514/317; 514/408; 514/569; 514/649; 514/731; 514/874; 514/899
[58] Field of Search ............ 514/227, 317, 408, 569, 514/646, 731, 899, 874

[56] References Cited

U.S. PATENT DOCUMENTS 4,820,736  4/1989  Jensen et al. ................. 514/651

FOREIGN PATENT DOCUMENTS 853072981  11/1985  European Pat. Off.

OTHER PUBLICATIONS

Endocrinol. Japon., vol. 23, No. 2, 1976, pp. 115–118. T. Hashimoto et al.: "Dual Effect of Clomiphene Citrate on Pituitary Gonadotropin Secretion in Postmenopausal Women", *Whole Article*.
J. Clin. Endocrinol. Metab., vol. 42, No. 3, 1976, pp. 593–594.
T. Hashimoto et al.: "Effect of Clomiphene Citrate on Basal and LHR-Induced Gonadotropin Secretion in Postmenopausal Women", *Whole Article*.
Neuroendocrinol. Lett., vol. 4, No. 6, 1982, pp. 377–381, Verlag Chemie GmbH, Weinheim, DE.
J. A. Moguilevsky et al.: "Effect of Clomiphene Citrate on LH, FSH and Estradiol Levels in Postmenopausal Women", *Whole Article*.
Ann. Endocrinol., vol. 38, No. 6, 1977, pp. 363–365, Paris, FR M. Pugeat et al.: "Effects du Citrate de Clomiphene et des Oestrogenes sur les Taux Plasmatiques des Gonadotrophines, Testosterone, Androstenedione Chez les Femmes Agees Menopausees", *Summary*.
Munchener Med. Wochenschrift, vol. 112, No. 51, 18th Dec. 1970, pp. 2303–2312, Munich, DE.
P. Franchimont: "Gonadotropin-Sekretion beim Menschen", *p. 2307*.
Martindale, The Extra Pharmacopoeia, 28th Edition, 1982, p. 140, Edited by J. E. F. Reynolds, The Pharmaceutical Press, London, GB *Monograph 9037–9039*.
Z. Artzl. Fortbild. (Jena), vol. 68, No. 15, 1974, pp. 796–801, W. Mobius: "Die Moderne Behandlung Klimakterischer Beschwerden", *p. 800, right-hand column, lines 4–8*.
Drug & Therapeutics Bulletin, vol. 16, No. 4, 17th Feb. 1978, pp. 13–16, "Management of the Menopause", *p. 14, last paragraph*.
Cah Med. Lyon, vol. 50, nr. 14, 1974, pp. 1227–1229, G. Tanne: "Le praticien devant . . . la menopause", *p. 1228*.
Acta Obstet. Gynec. Scand., vol. 54, No. Suppl. 51, 1975, pp. 47–61, Ch. Lauritzen: "The Female Climacteric Syndrome: Significance, Problems, Treatment:", *p. 52, right-hand column, p. 53, table 5*.
Vie Med. Can. Fr., vol. 7, No. 3, 1978, pp. 217–223, Y. Ainmelk: "Pharmacotherapie de la Menopause", *p. 221*.
Concours Med., vol. 98, No. 8 Suppl. 1976, pp. 1–48.
J. A. Mahoudeau et al.: "Pathologie ovarienne", *p. 22*.
Beall et al, Calcif. Tissue Int'l. 36: 123–125, 1984.
Chem. Abst. 100:132789g, 1984.

*Primary Examiner*—John W. Rollins
*Attorney, Agent, or Firm*—Eric P. Mirabel; Ned L. Conley; David A. Rose

[57] ABSTRACT

Disclosed is a method for treating menopausal symptoms and treating and preventing osteoporosis, wherein a true antiestrogen is administered and estrogen is not. This treatment is effective for female osteoporosis and can also be used to treat male osteoporosis. Examples of true antiestrogens are clomiphene, and its isomers, citrates and derivatives, as well as several other compounds which appear in the specification.

15 Claims, No Drawings

ANTIESTROGENS AND THEIR USE IN TREATMENT OF MENOPAUSE AND OSTEOPOROSIS

RELATED APPLICATIONS

This application is a continuation-in-part of my application Ser. No. 660,510 which was filed on Oct. 12, 1984, now U.S. Pat. No. 4,729,999. I claim priority to that date.

FIELD OF THE INVENTION

The invention relates to the use of antiestrogens in treatment of menopausal symptoms and treatment and prevention of osteoporosis.

BACKGROUND OF THE INVENTION

In the United States alone, there are approximately 40 million women who have entered their postmenopausal years. The life expectancy of a woman who attains her last menstrual period is about 28 years. A recent study indicates that 75 to 85% of these postmenopausal women will develop symptoms of estrogen deficiency. C. Hammond, M.D., et al., "Current Status of Estrogen Therapy for the Menopause," *Fertil. Steril.*, 37(1): 5-25 (1982).

A common complaint of patients following ovarian failure is the "hot flash" or vasomotor symptom complex. This is described as a sudden onset of warmth in the face and neck, often progressing to the chest. It generally lasts several minutes, and is often evidenced by a visible red flush. These episodes may be uncomfortable. They are often accompanied by dizziness, nausea, headaches, palpitations and diaphoresis. Estrogen supplementation provides relief to over 90% of such patients.

Progressive atrophy of the genitourinary system commonly accompanies old age. It is related both to estrogen deprivation and to aging. The vagina, cervix, corpus uteri, fallopian tubes, urethra and bladder trigone all have large numbers of estrogen receptors and are sensitive to decreases in estrogen. The vagina exhibits atrophic changes from estrogen deprivation such as thinning of the epithelium, loss of rugation and a reduction in lubrication during sexual intercourse. Atrophic vaginitis accounts for approximately 15% of postmenopausal bleeding. It also contributes significantly to dyspareunia.

Atrophy of the urethra often accompanies similar changes in the vagina. Urethral atrophy often causes dysuria, frequent urination and urinary urgency. Systemic or intravaginal estrogen administration reverses this atrophy.

The most serious of all postmenopausal complications is osteoporosis. In women over 60 years of age, 25% have documented spinal compression fractures as a result of osteoporosis. As many as 50% of women will have developed vertebral fractures by age 75. The risk of hip fractures increases with age, reaching 20% by age 90. Eighty percent (80%) of hip fractures are felt to be related to pre-existing osteoporosis. Even more devastating is the fact that approximately one-sixth of women with hip fractures die within three months following their fracture. A Mayo Clinic study calculates the health care costs of fracture hospital stays at over $1,000,000,000 per year. J. Gallagher, et al., "Epidemiology of Fractures of the Proximal Femur in Rochester, Minn.," *Clin. Ortho.* 150: 163-171 (1980).

Although osteoporosis is relatively common in postmenopausal women, it can also occur in other estrogen deficient women and in males, in particular, in senile males. As is true for postmenopausal women, fractures associated with osteoporosis are a major problem for anyone suffering from it.

Current theories of the causes of postmenopausal osteoporosis include dietary factors and calcium intake, aging, genetic susceptibility, and Vitamin D levels. Theories of the hormonal control of bone deposition and absorption include roles for estrogen, androgens, parathyroid hormones, growth hormones and calcitonin. Current treatment for postmenopausal osteoporosis include fluoride, Vitamin D and calcium supplementation, increased physical activity and, as the primary choice, estrogen replacement therapy. The precise mechanism of the action of estrogen on bone metabolism is unknown. There are no estrogen receptors which have been identified in bone, and estrogen does not appear to stimulate osteoblastic activity. Estrogen therapy does not replace bone which has already been lost, and if discontinued, more rapid bone loss results.

Because of the potential severity and the frequency of postmenopausal complications, long-term estrogen replacement is a common practice. However, estrogen therapy has been implicated in a variety of disorders. The Boston Collaborative Drug Surveillance Program indicated a summary risk ratio for gall bladder disease in postmenopausal women taking estrogen of 2.5. Boston Collab. Drug Surv., "Surgically Confirmed Gallbladder Disease, Venous Thromboembolism, and Breast Tumors in Relation to Postmenopausal Estrogen Therapy." *N. Eng. J. Med.* 290: 15-19 (1974). Other studies have associated estrogen replacement with hypertension, abnormal glucose tolerance, hypercoagulability and arteriosclerosis, although these observations have not been confirmed. M. Crane, et al., "Hypertension, Oral Contraceptive Agents, and Conjugated Estrogens," *Ann. Int. Med.* 74(1): 13-21 (1971); R. Pfeffer, "Estrogen Use, Hypertension and Stroke in Postmenopausal Women," *J. Chron. Dis.* 31: 389-398 (1978); M. Notelovitz, "Metabolic Effect of Conjugated Oestrogens (USP) on Glucose Tolerance," *So. African Med. J.* 48(4): 2599-2603 (1974); J. Stangel, et al., "The Effect of Conjugated Estrogens on Coagulability in Menopausal Women," *Obstet. Gynecol.* 49(3): 314-316 (1977); T. Gordon, et al., "Menopause and Coronary Heart Disease," *Ann. Int. Med.* 89(2): 157-161 (1978).

Estrogen has also been suggested as a cause of benign breast disease. Estrogen receptors are known to be present in the breast. Estrogen may induce cystic or dysplastic changes in postmenopausal women, as demonstrated by mammography. Estrogen can also induce mammary tumors in animals, particularly in susceptible strains of mice and rats. Some breast cancers in women respond positively to oophorectomy, suggesting that estrogen may cause stimulation and maintenance of breast neoplasia.

Unopposed estrogenic stimulation has also been implicated in endometrial hyperplasia and endometrial carcinoma. Regular progestin administration appears to protect against endometrial cancer. However, postmenopausal women treated with estrogen-progestin combinations frequently experience regular and undesirable uterine bleeding. Thus, an alternative to estrogen therapy would be highly desirable.

There have been efforts to counteract the ill effects of estrogen therapy; for example, estrogen administration coupled with short periods of antiestrogen administration. See, A. Kauppila, et al., "Comparison of Megestrol Acetate and Clomiphene Citrate as Supplemental Medication in Postmenopausal Oestrogen Replacement Therapy,": *Arch. Gynecol.* 234: 49–58 (1983). In his study, Kauppila administered 1.25 mg/day conjugated oestrogens to postmenopausal women for 20 days. This was followed by a pause of 10 days. During every third pause, 10 mg of megestrol acetate was administered to one group and 50 mg of clomiphene citrate, U.S. Pat. No. 2,914,563, was administered to another group, daily for 10 days. See also U.S. Pat. Nos. 4,061,733; 2,914,562; 2,914,564; and 3,634,517. Similar tests, using conjugated estrogens with periods of clomiphene citrate administration, were reported by A. Kauppila, M.D., et al., "Postmenopausal Hormone Replacement Therapy With Estrogen Periodically Supplemented With Antiestrogen," *Am. J. Obstet. Gynecol.* 140(7): 787–792 (1981). See also A. J. Wise, et al., "Quantitative Relationships of the Pituitary-Gonadal Axis in Postmenopausal Women," *J. Lab. Clin. Med.*, 81(1): 28–36 (1973). In the Kauppila studies estrogen was used as the essence of the treatment and the antiestrogen(s) were to counteract estrogen's adverse effects.

Antigonadotropic agents substantially free of estrogenic effects have also been discovered. See, e.g., U.S. Pat. Nos. 3,843,727 and 3,697,581. However, these agents are not "true" antiestrogens inasmuch as they lack estrogenic effects.

It has been observed that some antiestrogens have estrogenic effects (the so-called "true" antiestrogens). See e.g., E. Su-Rong Huang & W. Miller, "Estrogenic and Antiestrogenic Effects of Enclomiphene and Zuclomiphene on Gonadotropin Secretion by Ovine Pituitary Cells in Culture," *Endocrinology* 112(2): 442–448 (1983); A. Mukku, et al., "Stimulatory and Inhibitory Effects of Estrogen and Antiestrogen on Uterine Cell Division," *Endocrinology* 109(4): 1005–10 (1981); M. Sankaran and M. Prasad, "A Critique on the Evaluation and Mode of Action of Antiestrogens," *Hormones and Antagonists Gynec. Invest.* 3: 143–47 (1972); L. Terenius and I. Ljungkvist, "Aspects on the Mode of Action of Antiestrogens and Antiprogestogens," *Hormones and Antagonists. Gynec. Invest.* 3: 96–107 (1972); C. Geynet, et al., "Estrogens and Antiestrogens," *Hormones and Antagonists. Gynec. Invest.* 3: 2–29 (1972); J. Wood, et al., "Estrogenic and Antiestrogenic Effects of Clomiphene, MER-25 and CN-55, 945-27 on the Rat Uterus and Vagina," *Endocrinol.* 82: 69–74 (1968); K. Schulz et al., "Studies on Anti-Oestrogenic and Oestrogen-Like Action of Clomiphene Citrate—Animal Experiments," *Hormones and Antagonists. Gynec. Invest.* 3: 135–141 (1972); J. Clark and B. Markaverich, "The Agonistic-Antagonistic Properties of Clomiphene: A Review," *Pharmac. Ther.* 15: 467–519 (1982). See also, M. Pugeat, et al., "On Testing The Threshold of Sensitivity of the Gonadostat in the Late Menopausal Period: Effect of the Administration of Clomiphene Citrate or Ethynylestradiol on Plasma Levels of Gonadotropin, Testosterone and Delta-4 Androstendione," *Eur. J. Obstet. Gynecol. Reprod. Biol.* 9(3): 218–219 (1979); M. Zambrano, et al., "Evaluation of the Action of Clomiphene Citrate (Clomid) on Mouse Chromosomes by the Metaphase and Micronucleus Tests," *Rev. Brasil. Genet.* 2: 339–344 (1982); J. Gennes, et al., "Clinical, Biological, Histological and Genetic Studies of De Morsier's Syndrome (Hypogonadotrophic Hypogonadism With Anosmia)," *Ann. Endrocrinol.* 31(5): 841–861 (1970); I. Spitz, et al., "The Decreased Basal and Stimulated Prolactin Levels in Isolated Gonadotrophin Deficiency: A Consequence of the Low Oestrogen State," *Clinical Endocrinology* 16: 423–432 (1982); S. Aksel, M.D., and G. Jones, M.D., "Etiology and Treatment of Dysfunctional Uterine Bleeding," *J. Obstet. and Gynec.* 44(1): 1–13 (1974); T. Hashimoto, M.D., et al., "Endocrinological Study of Patients With Meningitis Tuberculosa," *Jap. J. Med.* 20(1): 45–49 (1981); and, C. March, M.D., "Effect of Pretreatment with Clomiphene Citrate Upon Human Menopausal Gonadotropin Therapy for Anovulation," *Fertil. Steril.* 26(2): 191–192 (1975). But the relevant studies have focused on the effects of antiestrogen administration on gonadotropins, rather than the effect of treatment of menopausal symptoms. See, e.g., T. Nencioni, et al., "Plasma FSH, LH and Prolactin Levels in Postmenopausal Women Undergoing Cyclofenil [sic.] Treatment," *Acta Obstet, Gynecol. Scand.* 61: 487–90 (1982); R. Young, et al., "Antiestrogen Effects on Gonadotropins and Uterus in the Ovariectomized Rat," *Abstracts of the Endocrine Society* #142, p. 108 (1979); M. Pugeat, et al., "Effects of Clomiphene and Estrogens on Circulating Gonadotropins, Testosterone, Androstenedione, in Old Menopausal Women," *Ann. Endocrinol.* 38: 363–65 (1977); T. Hashimoto et al., "Dual Effect of Clomiphene Citrate on Pituitary Gonadotropin Secretion in Postmenopausal Women," *Endocrinol. Jap.* 23(2): 115–18 (1976). One group has also studied the effects of the antiestrogen clomiphene on total body calcium in rats. A. LeBlanc, et al., "Effects of Clomiphene on Total Body Calcium in Aged Oophorectomized Rats," *Calcium, Calcium Hormones,* Abstract #7738, p. 1594 (1982). In fact, in an article reviewing all studies to that date on the antiestrogen clomiphene, its use in treatment of menopausal symptoms was expressly contra-indicated. J. Clark, et al., "The Agonistic-Antagonistic Properties of Clomiphene: A Review," *Pharmac. Ther.* 15: 467–519 (1982).

In conclusion, no one has taught or suggested use of antiestrogens to treat menopausal symptoms or osteoporosis.

SUMMARY OF THE INVENTION

It has been discovered that administering "true" antiestrogens can effectively treat menopausal symptoms, and/or the symptoms caused by induced or uninduced estrogen deficiency. There is also data indicating that administration of true antiestrogens is effective in treating osteoporosis, both in the male and the female.

True antiestrogens are those which bind estrogen receptors in competition with estrogens, and yet exhibit some estrogenic activity. If estrogen is present, a true antiestrogen inhibits estrogenic activity. In the progressive absence of estrogen, true antiestrogens become increasingly estrogenic.

With the compounds of the invention it is not necessary to simultaneously administer estrogen to treat menopause. This is a substantial advantage, particularly for those patients who are estrogen intolerant. In the event that there is some endogenous estrogen production, many true antiestrogens aid in treatment of estrogen side effects. This is another advantage of antiestrogen administration. The preferred method of carrying out the true antiestrogen administration is described below.

DESCRIPTION OF THE PREFERRED EMBODIMENTS

A true antiestrogen, preferably clomiphene, is administered to an estrogen deficient subject, e.g., a postmenopausal or oophorectomized woman. Alternatively, it can be administered to a male with osteoporosis, senile or otherwise. The antiestrogen is given on a regular basis, usually daily, and over an extended period. The preferred daily dosage is 0.4 to 3.0 micromoles/kg of body weight; most preferably, 0.7 to 2.0 micromoles/kg of body weight. If clomiphene is the antiestrogen, the daily dose for women is preferably 12.5 to 100 mg., and most preferably is 12.5 to 25.0 mg, whereas the preferred dosage for senile men is 12.5 to 50 mg/day. Oral administration is preferred, though other modes, e.g. injection, nasal, buccal, aural or ocular administration, are also contemplated. The true antiestrogens of the invention include the following:

Clomiphene, zuclomiphene, enclomiphene, and citrates thereof. Other derivatives of clomiphene can also be used;

Cycladiene, Merck Index, 10th ed. #3085 and U.S. Pat. No. 2,464,203 and U.S. Pat. No. 2,465,505, incorporated herein by reference;

Tamoxifen, Merck Index, 10th ed. #8923, incorporated herein by reference;

Nafoxidine, USAN and USP Dictionary of Drug Names, p. 327 (1983), incorporated herein by reference;

CI-680, Unlisted Drugs, 28(10): 169(o) (1976), incorporated herein by reference;

CI-628, Unlisted Drugs, 26(7): 106(l) (1974), incorporated herein by reference;

CN-55,945-27, or nitromifene citrate, Unlisted Drugs, 27(12): 194(n) (1975), incorporated herein by reference;

R2323 or 13-ethyl-17a-ethynl-17B-hydroxygona-4,9,11-trien-3-one, Unlisted Drugs, 23(3): 34(b) (1971), incorporated herein by reference;

MER-25; U-11,555A; U-11,100A; ICI-46,669 and ICI-46,474; all shown in L. Terenius, et al., "Aspects on the Mode of Action of Antiestrogens and Antiprogestrogens," *Hormones and Antagonists. Gynec. Invest.* 3: 98, incorporated herein by reference;

Compounds having the formula:

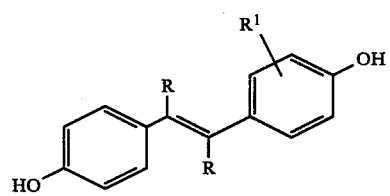

wherein $R_1$ can be hydrogen, an aromatic group or an alkyl group, the alkyl group preferably having no more than 9 carbon atoms, and R can be an aromatic group or an alkyl group, the alkyl group preferably having no more than 9 carbon atoms, the derivatives of this invention including only those derivatives exhibiting true antiestrogenic effects and not including diethylstilbestrol, wherein both R's are an ethyl group, and $R_1$ is a hydrogen group;

Diphenol hydrochrysene; erythro-MEA; and Park Davis CN-55,945; all disclosed in C. Geynet, et al., "Estrogens and Antiestrogens," *Hormones and Antag-*

*onists. Gynec. Invest.* 3: 12–13 (1972), incorporated herein by reference;

Allenolic acid and cyclofenyl, disclosed in C. Geynet, et al., *Hormones and Antagonists. Gynec. Invest.* 3: 17 (1972), incorporated herein by reference;

Chlorotrianisene, Merck Index, 10th ed., #2149, incorporated herein by reference;

Ethamoxytriphetol, Merck Index, 10th ed., #3668, incorporated herein by reference;

Triparanol, Merck Index, 10th ed., #9541 and U.S. Pat. No. 2,914,562, incorporated herein by reference; or Any of the triphenyl compounds shown in U.S. Pat. No. 2,914,563, hereby incorporated by reference, which discloses compounds having the formula

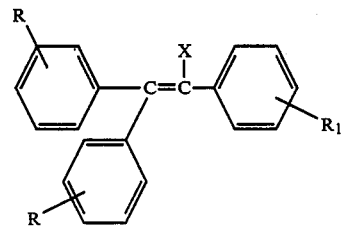

wherein one of the R's is a basic ether of the formula —$OC_nH_{2n}$—A wherein n is 2, 3 or 4, and A is a dialkylamino group of 1–4 carbon atoms or N-piperidyl or B-morphylinyl, and the other R and $R_1$ are hydrogen, halogen or methoxy and X is halogen.

These true antiestrogen compounds are all believed to have a common mode of action. See M. Sankaran and M. Prasad, "A Critique on the Evaluation and Mode of Action of Antiestrogens," *Hormones and Antagonists. Gynec. Invest.* 3: 142–147 (1972), and L. Terenius and I. Ljungkvist, "Aspects on the Mode of Action of Antiestrogens and Antiprogestogens," *Hormones and Antagonists. Gynec. Invest.* 3: 96–107 (1972). Physiologically acceptable forms of any of these true antiestrogens, e.g., acid salts such as citrates, can be administered. In addition, excipients, or optional ingredients, e.g., fillers, perfumes, colorants, sweetners and carriers, can be used with the dosage form of the antiestrogens.

Clinical trials comparing results achieved with administration of clomiphene and Premarin (a conjugated equine estrogen), are set forth below.

EXAMPLE 1

A clinical trial was conducted in which the effect of Premarin administration in post-menopausal women was compared with clomiphene administration. The effects of both drugs were compared by comparing various standard indicia related to menopause. The results are tabulated below for each patient which completed the study.

Three months prior to beginning the study, each patient stopped taking all forms of estrogen. The "Baseline" values were taken at the end of this three month period, and before beginning administration of clomiphene or Premarin. The patients were seen at baseline and three months, and lab tests were run when the patients were seen and at three weeks and six weeks. Clomiphene patients were started out on a dose of 12.5 mg/day, which was increased to 25 mg/day, if needed. However, dosages up to 100 mg/day can be used. Twenty-two patients began the study, but three were dropped, leaving a total of nineteen, or ten clomiphene patients and nine Premarin patients.

PATIENT 1
Administered 12.5 mg of clomiphene citrate per day.

|  | Baseline | 3-Months |
|---|---|---|
| Serum FSH (MIU/ml) | 145 | 102 |
| Urinary Estrogen (ug/24°) | 32 | 26 |
| Urinary Hydroxyproline (mg/24°) | 37 | 34 |
| Creatinine Clearance | 1.36 m/24° (urine) 0.9 mg/dl (serum) | 1.46 m/24° (urine) 1.1 mg/dl (serum) |
| Serum Cholesterol (mg/dl) | 181 | 219 |
| Serum HDL (mg/dl) | 40 | 44 |
| Serum Fibrinogen (mg/dl) | 260 | 350 |

|  | Baseline | 1-Month | 2-Months | 3-Months |
|---|---|---|---|---|
| Kupperman Index | 20 | 7 | 10 | 9 |
|  | Baseline | 3-Weeks | 6-Weeks | 3-Months |
| Ionized Calcium (mmo/l) | 1.25 | 1.26 | 1.24 | 1.25 |
| Parathyroid Hormone (nleq/l) | 170 | 191 | 169 | 173 |

PATIENT 2
Administered 12.5 mg (increased to 25 mg) of clomiphene citrate per day.

|  | Baseline | 3-Months |
|---|---|---|
| Serum FSH (MIU/ml) | 187 | 128 |
| Urinary Estrogen (ug/24°) | 50 | 20 |
| Urinary Hydroxyproline (mg/24°) | 38 | 29 |
| Creatinine Clearance | 1.16 m/24° (urine) 0.9 mg/dl (serum) | 1.16 m/24° (urine) 0.9 mg/dl (serum) |
| Serum Cholesterol (mg/dl) | 192 | 168 |
| Serum HDL (mg/dl) | 51 | 60 |
| Serum Fibrinogen (mg/dl) | 390 | 275 |

|  | Baseline | 1-Month | 2-Months | 3-Months |
|---|---|---|---|---|
| Kupperman Index | 10 | 10 | 10 | 11 |
|  | Baseline | 3-Weeks | 6-Weeks | 3-Months |
| Ionized Calcium (mmo/l) | 1.32 | 1.24 | 1.38 | 1.30 |
| Parathyroid Hormone (nleq/l) | 141 | 117 | 121 | 151 |

PATIENT 3
Administered 12.5 mg (increased to 25 mg) of clomiphene citrate per day.

|  | Baseline | 3-Months |
|---|---|---|
| Serum FSH (MIU/ml) | 130 | 105 |
| Urinary Estrogen (ug/24°) | 6 | 25 |
| Urinary Hydroxyproline (mg/24°) | 27 | 23 |
| Creatinine Clearance | 0.9 g/24° (urine) 0.8 mg/dl (serum) | 0.7 g/24° (urine) 0.9 mg/dl (serum) |
| Serum Cholesterol (mg/dl) | 229 | 182 |
| Serum HDL (mg/dl) | 49 | 47 |
| Serum Fibrinogen (mg/dl) | 495 | 540 |

|  | Baseline | 1-Month | 2-Months | 3-Months |
|---|---|---|---|---|
| Kupperman Index | 31 | 15 | 13 | 7 |
|  | Baseline | 3-Weeks | 6-Weeks | 3-Months |
| Ionized Calcium (mmo/l) | 1.25 | 1.25 | 1.31 | 1.27 |
| Parathyroid Hormone (nleq/l) | 137 | 114 | 95 | 100 |

PATIENT 4
Administered 12.5 mg (increased to 25 mg) of clomiphene citrate per day.

|  | Baseline | 3-Months |
|---|---|---|
| Serum FSH (MIU/ml) | 129 | 95 |
| Urinary Estrogen (ug/24°) | 8.2 | 17 |
| Urinary Hydroxyproline (mg/24°) | 31 | 42 |
| Creatinine Clearance | 1.6 g/24° (urine) 1.0 mg/dl (serum) | 1.0 g/24° (urine) 0.9 mg/dl (serum) |
| Serum Cholesterol (mg/dl) | 281 | 222 |
| Serum HDL (mg/dl) | 61 | 51 |
| Serum Fibrinogen (mg/dl) | 320 | 340 |

|  | Baseline | 1-Month | 2-Months | 3-Months |
|---|---|---|---|---|
| Kupperman Index | 19 | 16 | 9 | 5 |
|  | Baseline | 3-Weeks | 6-Weeks | 3-Months |
| Ionized Calcium (mmo/l) | 1.24 | 1.29 | 1.24 | 1.22 |
| Parathyroid Hormone (nleq/l) | 145 | 153 | 164 | 217 |

PATIENT 5
Administered 12.5 mg (increased to 25 mg) of clomiphene citrate per day.

|  | Baseline | 3-Months |
|---|---|---|
| Serum FSH (MIU/ml) | 110 | 8 |
| Urinary Estrogen (ug/24°) | 19 | 134 |
| Urinary Hydroxyproline (mg/24°) | 32 | 23 |
| Creatinine Clearance | 0.7 g/24° (urine) 0.9 mg/dl (serum) | 1.1 g/24° (urine) 0.8 mg/dl (serum) |
| Serum Cholesterol (mg/dl) | 188 | 181 |
| Serum HDL (mg/dl) | 48 | 48 |
| Serum Fibrinogen (mg/dl) | 310 | 175 |

|  | Baseline | 1-Month | 2-Months | 3-Months |
|---|---|---|---|---|
| Kupperman Index | 10 | 19 | 16 | 24 |
|  | Baseline | 3-Weeks | 6-Weeks | 3-Months |
| Ionized Calcium (mmo/l) | 1.23 | 1.22 | 1.16 | 1.18 |
| Parathyroid Hormone (nleq/l) | 178 | 153 | 179 | 168 |

PATIENT 6
Administered 12.5 mg (increased to 25 mg) of clomiphene citrate per day.

|  | Baseline | 3-Months |
|---|---|---|
| Serum FSH (MIU/ml) | 22 | 89 |
| Urinary Estrogen (ug/24°) | 54 | 85 |
| Urinary Hydroxyproline (mg/24°) | 13 | 17 |
| Creatinine Clearance | 0.9 g/24° (urine) 0.7 mg/dl (serum) | 1.0 g/24° (urine) 0.7 mg/dl (serum) |
| Serum Cholesterol (mg/dl) | 194 | 191 |
| Serum HDL (mg/dl) | 46 | 44 |
| Serum Fibrinogen (mg/dl) | 370 | 255 |

|  | Baseline | 1-Month | 2-Months | 3-Months |
|---|---|---|---|---|
| Kupperman Index | 22 | 14 | 18 | 14 |
|  | Baseline | 3-Weeks | 6-Weeks | 3-Months |
| Ionized Calcium (mmo/l) | 1.14 | 1.20 | 1.18 | 1.13 |
| Parathyroid Hormone | 173 | 143 | 148 | 166 |

-continued (nleq/l)

PATIENT 7
Administered 12.5 mg (increased to 25 mg) of clomiphene citrate per day.

|  | Baseline | 3-Months |
|---|---|---|
| Serum FSH (MIU/ml) | 116 | 109 |
| Urinary Estrogen (ug/24°) | 40 | 31 |
| Urinary Hydroxyproline (mg/24°) | 53 | 61 |
| Creatinine Clearance | 1.2 g/24° (urine) 0.8 mg/dl (serum) | 1.2 g/24° (urine) 0.8 mg/dl (serum) |
| Serum Cholesterol (mg/dl) | 171 | 19.9 |
| Serum HDL (mg/dl) | 43 | 52 |
| Serum Fibrinogen (mg/dl) | 480 | 275 |

|  | Baseline | 1-Month | 2-Months | 3-Months |
|---|---|---|---|---|
| Kupperman Index | 28 | 18 | 20 | 21 |
|  | Baseline | 3-Weeks | 6-Weeks | 3-Months |
| Ionized Calcium (mmo/l) | 1.26 | 1.21 | 1.20 | 1.21 |
| Parathyroid Hormone (nleq/l) | 77 | 90 | 41 | 74 |

PATIENT 8
Administered 12.5 mg (increased to 25 mg) of clomiphene citrate per day.

|  | Baseline | 3-Months |
|---|---|---|
| Serum FSH (MIU/ml) | 139 | 77 |
| Urinary Estrogen (ug/24°) | 9 | 27 |
| Urinary Hydroxyproline (mg/24°) | 40 | 25 |
| Creatinine Clearance | 1.0 g/24° (urine) 1.1 mg/dl (serum) | 1.0 g/24° (urine) 1.0 mg/dl (serum) |
| Serum Cholesterol (mg/dl) | 165 | 207 |
| Serum HDL (mg/dl) | 38 | 46 |
| Serum Fibrinogen (mg/dl) | 330 | 250 |

|  | Baseline | 1-Month | 2-Months | 3-Months |
|---|---|---|---|---|
| Kupperman Index | 42 | 38 | 41 | 39 |
|  | Baseline | 3-Weeks | 6-Weeks | 3-Months |
| Ionized Calcium (mmo/l) | 1.27 | 1.23 | 1.26 | 1.25 |
| Parathyroid Hormone (nleq/l) | 173 | 150 | 160 | 125 |

PATIENT 9
Administered 12.5 mg (increased to 25 mg) of clomiphene citrate per day.

|  | Baseline | 3-Months |
|---|---|---|
| Serum FSH (MIU/ml) | 127 | 113 |
| Urinary Estrogen (ug/24°) | 32 | 18 |
| Urinary Hydroxyproline (mg/24°) | 30 | 14 |
| Creatinine Clearance | 1.56 g/24° (urine) 1.0 mg/dl (serum) | 1.1 g/24° (urine) 1.2 mg/dl (serum) |
| Serum Cholesterol (mg/dl) | 229 | 232 |
| Serum HDL (mg/dl) | 44 | 60 |
| Serum Fibrinogen (mg/dl) | 265 | 245 |

|  | Baseline | 1-Month | 2-Months | 3-Months |
|---|---|---|---|---|
| Kupperman Index | 23 | 21 | 11 | 16 |
|  | Baseline | 3-Weeks | 6-Weeks | 3-Months |
| Ionized Calcium (mmo/l) | 1.20 | 1.20 | 1.18 | 1.16 |
| Parathyroid Hormone | 162 | 162 | 180 | 186 |

(nleq/l)

PATIENT 10
Administered 12.5 mg of clomiphene citrate per day.

|  | Baseline | 3-Months |
|---|---|---|
| Serum FSH (MIU/ml) | 104 | 105 |
| Urinary Estrogen (ug/24°) | 4 | 5 |
| Urinary Hydroxyproline (mg/24°) | 20 | 15 |
| Creatinine Clearance | 0.6 g/24° (urine) 0.6 mg/dl (serum) | 0.8/24° (urine) 0.8 mg/dl (serum) |
| Serum Cholesterol (mg/dl) | 160 | 153 |
| Serum HDL (mg/dl) | 36 | 55 |
| Serum Fibrinogen (mg/dl) | 260 | 160 |

|  | Baseline | 1-Month | 2-Months | 3-Months |
|---|---|---|---|---|
| Kupperman Index | 28 | 21 | 13 | 17 |
|  | Baseline | 3-Weeks | 6-Weeks | 3-Months |
| Ionized Calcium (mmo/l) | 1.06 | 1.16 | 1.17 | 1.23 |
| Parathyroid Hormone (nleq/l) | 157 | 140 | 131 | 105 |

PATIENT 11
Administered 0.625 mg of Premarin per day.

|  | Baseline | 3-Months |
|---|---|---|
| Serum FSH (MIU/ml) | 112 | 90 |
| Urinary Estrogen (ug/24°) | 47 | 9 |
| Urinary Hydroxyproline (mg/24°) | 37 | 25 |
| Creatinine Clearance | 1.66 m/24° (urine) 0.8 mg/dl (serum) | 1.16 m/24° (urine) 0.8 mg/dl (serum) |
| Serum Cholesterol (mg/dl) | 152 | 177 |
| Serum HDL (mg/dl) | 39 | 50 |
| Serum Fibrinogen (mg/dl) | 340 | 370 |

|  | Baseline | 1-Month | 2-Months | 3-Months |
|---|---|---|---|---|
| Kupperman Index | 31 | 39 | 34 | 27 |
|  | Baseline | 3-Weeks | 6-Weeks | 3-Months |
| Ionized Calcium (mmo/l) | 1.30 | 1.25 | 1.31 | 1.30 |
| Parathyroid Hormone (nleq/l) | 76 | 87 | 91 | 72 |

PATIENT 12
Administered 0.625 mg of Premarin per day.

|  | Baseline | 3-Months |
|---|---|---|
| Serum FSH (MIU/ml) | 110 | 91 |
| Urinary Estrogen (ug/24°) | 78 | 21 |
| Urinary Hydroxyproline (mg/24°) | 41 | 40 |
| Creatinine Clearance | 1.5 g/24° (urine) 0.9 mg/dl (serum) | 1.3 g/24° (urine) 0.9 mg/dl (serum) |
| Serum Cholesterol (mg/dl) | 213 | 217 |
| Serum HDL (mg/dl) | 71 | 84 |
| Serum Fibrinogen (mg/dl) | 175 | 260 |

|  | Baseline | 1-Month | 2-Months | 3-Months |
|---|---|---|---|---|
| Kupperman Index | 20 | 11 | 8 | 4 |
|  | Baseline | 3-Weeks | 6-Weeks | 3-Months |
| Ionized Calcium (mmo/l) | 1.22 | 1.22 | 1.26 | 1.24 |
| Parathyroid Hormone (nleq/l) | 115 | 91 | 113 | 106 |

PATIENT 13
Administered 0.625 mg of Premarin per day.

-continued

|  | Baseline | 3-Months |
|---|---|---|
| Serum FSH (MIU/ml) | 114 | 85 |
| Urinary Estrogen (ug/24°) | 27 | (lost specimen) |
| Urinary Hydroxyproline (mg/24°) | 30 | 44 |
| Creatinine Clearance | 1.0 g/24° (urine) 0.9 mg/dl (serum) | 0.8 g/24° (urine) 0.9 mg/dl (serum) |
| Serum Cholesterol (mg/dl) | 206 | 195 |
| Serum HDL (mg/dl) | 62 | 70 |
| Serum Fibrinogen (mg/dl) | 330 | 250 |

|  | Baseline | 1-Month | 2-Months | 3-Months |
|---|---|---|---|---|
| Kupperman Index | 21 | 2 | 9 | 7 |
|  | Baseline | 3-Weeks | 6-Weeks | 3-Months |
| Ionized Calcium (mmo/l) | 1.33 | 1.31 | 1.27 | 1.25 |
| Parathyroid Hormone (nleq/l) | 168 | 153 | 154 | 151 |

PATIENT 14
Administered 0.625 mg of Premarin per day.

|  | Baseline | 3-Months |
|---|---|---|
| Serum FSH (MIU/ml) | 128 | 5 |
| Urinary Estrogen (ug/24°) | 8.4 | 220 |
| Urinary Hydroxyproline (mg/24°) | 29 | 15 |
| Creatinine Clearance | 1.36 m/24° (urine) 0.9 mg/dl (serum) | 1.1 g/24° (urine) 0.9 mg/dl (serum) |
| Serum Cholesterol (mg/dl) | 141 | 118 |
| Serum HDL (mg/dl) | 23 | 27 |
| Serum Fibrinogen (mg/dl) | 270 | 195 |

|  | Baseline | 1-Month | 2-Months | 3-Months |
|---|---|---|---|---|
| Kupperman Index | 12 | 15 | 18 | 12 |
|  | Baseline | 3-Weeks | 6-Weeks | 3-Months |
| Ionized Calcium (mmo/l) | 1.24 | 1.18 | 1.16 | 1.19 |
| Parathyroid Hormone (nleq/l) | 142 | 119 | 111 | 89 |

PATIENT 15
Administered 0.625 mg of Premarin per day.

|  | Baseline | 3-Months |
|---|---|---|
| Serum FSH (MIU/ml) | 103 | 98 |
| Urinary Estrogen (ug/24°) | 58 | 125 |
| Urinary Hydroxyproline (mg/24°) | 39 | 23 |
| Creatinine Clearance | 1.6 g/24° (urine) 1.0 mg/dl (serum) | 1.3 g/24° (urine) 1.0 mg/dl (serum) |
| Serum Cholesterol (mg/dl) | 234 | 232 |
| Serum HDL (mg/dl) | 48 | 48 |
| Serum Fibrinogen (mg/dl) | 280 | 295 |

|  | Baseline | 1-Month | 2-Months | 3-Months |
|---|---|---|---|---|
| Kupperman Index | 32 | 31 | 22 | 33 |
|  | Baseline | 3-Weeks | 6-Weeks | 3-Months |
| Ionized Calcium (mmo/l) | 1.25 | 1.20 | 1.22 | 1.23 |
| Parathyroid Hormone (nleq/l) | 90 | 101 | 99 | 69 |

PATIENT 16
Administered 0.625 mg of Premarin per day.

|  | Baseline | 3-Months |
|---|---|---|
| Serum FSH (MIU/ml) | 78 | 46 |
| Urinary Estrogen (ug/24°) | 5 | 52 |
| Urinary Hydroxyproline (mg/24°) | 26 | 13 |
| Creatinine Clearance | 1.5 g/24° (urine) 1.0 mg/dl (serum) | 1.7 g/24° (urine) 0.9 mg/dl (serum) |
| Serum Cholesterol (mg/dl) | 299 | 256 |
| Serum HDL (mg/dl) | 39 | 55 |
| Serum Fibrinogen (mg/dl) | 355 | 400 |

|  | Baseline | 1-Month | 2-Months | 3-Months |
|---|---|---|---|---|
| Kupperman Index | 24 | 12 | 12 | 15 |
|  | Baseline | 3-Weeks | 6-Weeks | 3-Months |
| Ionized Calcium (mmo/l) | 1.38 | 1.36 | 1.27 | 1.33 |
| Parathyroid Hormone (nleq/l) | 173 | 121 | 128 | 122 |

PATIENT 17
Administered 0.625 mg of Premarin per day.

|  | Baseline | 3-Months |
|---|---|---|
| Serum FSH (MIU/ml) | 134 | 68 |
| Urinary Estrogen (ug/24°) | 110 | 112 |
| Urinary Hydroxyproline (mg/24°) | 29 | 23 |
| Creatinine Clearance | 1.2 g/24° (urine) 1.1 mg/dl (serum) | 1.36 g/24° (urine) 0.9 mg/dl (serum) |
| Serum Cholesterol (mg/dl) | 204 | 221 |
| Serum HDL (mg/dl) | 38 | 54 |
| Serum Fibrinogen (mg/dl) | 390 | 330 |

|  | Baseline | 1-Month | 2-Months | 3-Months |
|---|---|---|---|---|
| Kupperman Index | 24 | 8 | 15 | 10 |
|  | Baseline | 3-Weeks | 6-Weeks | 3-Months |
| Ionized Calcium (mmo/l) | 1.38 | 1.36 | 1.27 | 1.37 |
| Parathyroid Hormone (nleq/l) | 178 | 165 | 209 | 174 |

PATIENT 18
Administered 0.625 mg of Premarin per day.

|  | Baseline | 3-Months |
|---|---|---|
| Serum FSH (MIU/ml) | 11 | 22 |
| Urinary Estrogen (ug/24°) | 22 | 66 |
| Urinary Hydroxyproline (mg/24°) | 18 | 22 |
| Creatinine Clearance | 0.9 g/24° (urine) 1.0 mg/dl (serum) | 0.9 g/24° (urine) 0.9 mg/dl (serum) |
| Serum Cholesterol (mg/dl) | 217 | 235 |
| Serum HDL (mg/dl) | 28 | 57 |
| Serum Fibrinogen (mg/dl) | 350 | 240 |

|  | Baseline | 1-Month | 2-Months | 3-Months |
|---|---|---|---|---|
| Kupperman Index | 19 | 23 | 12 | 11 |
|  | Baseline | 3-Weeks | 6-Weeks | 3-Months |
| Ionized Calcium (mmo/l) | 1.12 | 1.14 | 1.13 | 1.17 |
| Parathyroid Hormone (nleq/l) | 244 | 199 | 180 | 221 |

PATIENT 19
Administered 0.625 mg of Premarin per day.

|  | Baseline | 3-Months |
|---|---|---|
| Serum FSH (MIU/ml) | 318 | 186 |
| Urinary Estrogen (ug/24°) | 14 | 117 |
| Urinary Hydroxyproline | 6 | 13 |

|  | -continued | |
| --- | --- | --- |
| (mg/24°) | | |
| Creatinine Clearance | 0.26 m/24° (urine) | 0.76 m/24° (urine) |
|  | 1.0 mg/dl (serum) | 1.1 mg/dl (serum) |
| Serum Cholesterol (mg/dl) | 225 | 241 |
| Serum HDL (mg/dl) | 35 | 43 |
| Serum Fibrinogen (mg/dl) | 165 | 270 |

|  | Baseline | 1-Month | 2-Months | 3-Months |
| --- | --- | --- | --- | --- |
| Kupperman Index | 26 | 23 | 8 | 10 |
|  | Baseline | 3-Weeks | 6-Weeks | 3-Months |
| Ionized Calcium (mmo/l) | 1.22 | 1.22 | 1.22 | 1.23 |
| Parathyroid Hormone (nleq/l) | 140 | 120 | 138 | 140 |

For all the patients tested, the following indices were also monitored.

PARTIAL THROMBOPLASTIN TIME

No significant change occurred with clomiphene citrate therapy (from $21\pm1.6$ before treatment to $21.1\pm1.4$ after treatment).

There was a significant increase with Premarin therapy (from $20.4\pm0.99$ before treatment to $26.5\pm2.7$. p less than 0.025 after treatment).

HYDROXYPROLINE/CREATININE RATIO

The decrease in ratio was greater on clomiphene citrate therapy (pre: $32.8\pm9.5$ vs. post: $29.4\pm11.36$) as compared with Premarin ($24.8\pm3.98$ vs. $23\pm13.6$, p less than 0.05).

PROTHROMBIN TIME

The patients showed no significant change in prothrombin time on either therapy regime.

ANALYSIS OF RESULTS

The Kupperman Index monitors several symptoms of menopause, e.g., vasomotor complaints, paresthesia, insomnia, nervousness, melancholia, weakness or fatigue, palpitations and formication. These numbers should decrease with clomiphene administration if it is efficacious. A decrease was in fact seen in 8/10 of the clomiphene patients, compared with a decrease in 7/9 of the Premarian patients.

Serum levels of Follicular Stimulating Hormone (FSH), which is an indicator of estrogen suppression and is elevated in menopause, should be greater than 17 MIU/ml if the patent is menopausal. It was above the threshold in 9/10 clomiphene patients and in 7/9 Premarin patients.

The levels of urinary estrogen should be elevated after hormonal therapy, but the baseline should not be above 10 ug/24°. The level elevated over time in 7/10 clomiphene patients. The baseline value was, however, below 10/ug/24° in only 4/10 clomiphene patients. In the Premarin patients, 6/9 showed an elevated level. However, the baseline value was below 10 ug/24° in only 3/9 patients.

A decrease in urinary hydroxyproline, which is excreted during bone loss, may indicate a decrease in the bone loss which accompanies osteoporosis. The results should, however, be between 15 and 62 mg/24°.

Of the clomiphene patients, 6/10 showed a decrease in urinary hydroxyproline, while 6/9 of the Premarin patients showed a decrease.

Creatinine clearance is a test of kidney function and is related to the rate of calcium excretion. The urinary result should be from 1.0–2.0 m/24°, and the serum from 0.5–1.7 mg/dl. In 7/10 clomiphene patients, serum and urine results were normal at baseline and after three months. In 2/10 clomiphene patients, the urinary results were below normal limits at baseline, and then increased to within normal limits by the end of three months. In the remaining clomiphene patient, the result was below normal at baseline and then declined further.

In 6/9 of the Premarin patients, the serum and urinary results were normal at baseline and after three months. In 1/9 of the Premarin patient the serum result was normal and then declined, while in the remaining patients, it was below normal at baseline and after three months.

Serum cholesterol levels should be between 150 and 300 mg/dl. If cholesterol declines, this indicates a decline in total serum lipids—a result which means a lesser risk of heart and circulatory problems. In 9/10 of the clomiphene patients, the serum cholesterol was within normal limits, with 7/10 of these patients showing a decrease over the test period. With the Premarin patients, 8/9 were within normal limits, but only 5/9 showed a decrease over the test period.

Serum HDL (High Density Lipoprotein) is also an indicator of serum lipid content. The results should be from 30–75 mg/dl. In 10/10 of the clomiphene patients it was within normal limits. In 7/9 of the Premarin patients it was within normal limits.

Fibrogen is known to be increased by estrogen. The level increased in 3/10 of the clomiphene patients and in 5/9 of the Premarin patients.

Ionized calcium is an indicator of calcium level and therefore a low level indicates a probability, or a risk, of osteoporosis. See, e.g., J. A. Gudmundsson et al., "Increased Bone Turnover During Gonadotropin-Releasing Hormone Superagonist-Induced Ovulation Inhibition," 65 *Clinical Endocrinology and Metabolism* 159 (1987); R. J. Chetkowski, et al., "Biologic Effects of Transdermal Estradiol," 314 *New England Journal of Medicine* 1615 (1986). The level should be between 1.18 and 1.31 mmo/l. In 8/10 of the clomiphene patients the level was within normal limits after the test period. In 6/9 of the Premarin patients the level was within normal limits.

PTH (Parathyroid Hormone) influences bone reabsorption of calcium. Normal limits are from 75 to 210 nleq/l. It was within normal limits in 9/10 of the clomiphene patients and 7/9 of the Premarin patients.

Partial thromboplastin time is an index of blood clotting. The fact that it did not increase with clomiphene citrate therapy means that patients treated therewith are no more likely to bleed than controls.

The Hydroxyproline/Creatinine ratio test is a measure of turnover of bone metabolism. See R. J. Chetkowski, 314 *New England Journal of Medicine* at 1617. It can be seen that it decreased more with clomiphene citrate than with Premarin, indicating that the former is more effectively preserving bone tissue and combating osteoporosis.

CONCLUSION FROM RESULTS

It can be seen that clomiphene yields about the same positive results as does Premarin. Clomiphene is, therefore, as effective as Premarin in the treatment of menopause and the treatment of induced and uninduced states of estrogen deficiency. Of particular importance is that in the majority of the clomiphene patients, urinary hydroxyproline decreased, creatinine clearance was normal, the hydroxyproline/creatinine ratio decreased, ionized calcium was normal, and PTH was normal. These parameters are pertinent to the calcium and bone loss which can accompany osteoporosis—the most serious complication of menopause. The risk of osteoporosis apparently is, therefore, reduced by clomiphene administration.

These parameters would be expected to follow the same pattern if clomiphene was administered for a senile male. Therefore, clomiphene is expected to also be effective in treating male osteoporosis.

EXAMPLE 2

Using the same general procedure as in Example 1, clomiphene administration is replaced by administration of 12.5 to 100 mg/day of zuclomiphene citrate, the cis-isomer of clomiphene. Results similar to those of Example 1 are expected. That is, this compound should also exhibit much of the same estrogenic activity as Premarin and should combat the symptoms of menopause, estrogen deficiency and bone tissue loss which can lead to osteoporosis.

EXAMPLE 3

Using the same general procedure as in Example 1, 12.5 to 100 mg/day of clomiphene, or an isomer, citrate or derivative thereof, is administered to a male suffering from osteoporosis. It is expected that this will combat bone tissue loss and aid in treatment of male osteoporosis.

Administration of other true antiestrogens of the invention should also yield the same positive results.

The compounds and their method of use described above are exemplary only, and not to be construed as limitations on the scope of protection. The scope of protection is defined in the claims which follow, and includes all equivalents of the subject matter of the claims.

I claim:

1. A method of treating and preventing bone tissue loss or osteoporosis in a patient, comprising administering a true antiestrogen selected from the group consisting of clomiphene, an isomer of clomiphene, a citrate of clomiphene, a derivative of clomiphene, tamoxifen, nafoxidine, CI-680, CI-628, CN-55,956-27, MER-25, U-11,555A, U-11,100A, ICI-46,669, ICI-46,474, diphenolhydrochrysene, erythro-MEA, Parke Davis CN-35,945, allenolic acid, cyclofenil, ethamoxytriphetol, and triparanol to said patient, without concomitant estrogen administration.

2. A method of treating and preventing female osteoporosis, comprising administering a true antiestrogen selected from the group consisting of clomiphene, an isomer of clomiphene, a citrate of clomiphene, a derivative of clomiphene, tamoxifen, nafoxidine, CI-680, CI-628, CN-55,956-27, MER-25, U-11,555A, U-11,100A, ICI-46,669, ICI-46,474, diphenolhydrochrysene, erythro-MEA, Parke Davis CN-35,945, allenolic acid, cyclofenil, ethamoxytriphetol, and triparanol to a post-menopausal or estrogen deficient female, or a female with osteoporosis, without any concomitant estrogen administration.

3. A method of treating and preventing male osteoporosis comprising administering a true anti-estrogen selected from the group consisting of clomiphene, an isomer of clomiphene, a citrate of clomiphene, a derivative of clomiphene, tamoxifen, nafoxidine, CI-680, CI-628, CN-55,956-27, MER-25, U-11,555A, U-11,100A, ICI-46,669, ICI-46,474, diphenolhydrochrysene, erythro-MEA, Parke Davis CN-35,945, allenolic acid, cyclofenil, ethamoxytriphetol, and triparanol to a male with osteoporosis.

4. The method of claim 1, 2, or 3 wherein the dosage of said true antiestrogen and the length of time of its administration are sufficient to reduce the bone tissue loss.

5. The method of claim 1, 2, or 3 wherein the dosage of said true antiestrogen is from 0.4 to 3.0 micromoles per kilogram of body weight.

6. The method of claim 1, 2, or 3 wherein the dosage of said true antiestrogen is from 0.7 to 2.0 micromoles per kilogram of body weight.

7. The method of claim 1, 2, or 3 wherein the true antiestrogen is clomiphene, or an isomer, citrate, or derivative thereof.

8. The method of claim 7 wherein the dosage of clomiphene is from 12.5 to 100 mg/day.

9. The method of claim 7 wherein the dosage of clomiphene is from 12.5 to 25.0 mg/day.

10. The method of claim 1, 2, or 3 wherein the true antiestrogen is clomiphene citrate.

11. The method of claim 10 wherein the dosage of clomiphene citrate is from 12.5 to 100 mg/day.

12. A method of treating or preventing bone tissue loss or osteoporosis comprising administering a true antiestrogen to a patient, wherein said antiestrogen is a compound having the formula:

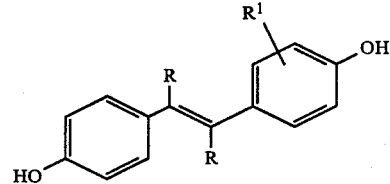

wherein $R_1$ is hydrogen, an aromatic group, or an alkyl group, and R is an aromatic group a methyl group, or an alkyl group with more than two carbon atoms in the chain.

13. A method of treating or preventing bone tissue loss or osteoporosis comprising administering a true antiestrogen to a patient, wherein said antiestrogen has the formula:

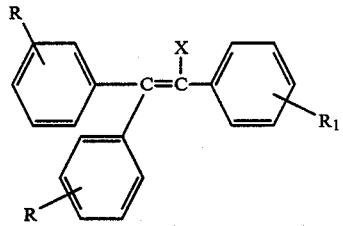

wherein one of the R's is a basic ether of the formula $-OC_nH_{2n}-A$, n is 2, 3, or 4, and A is a dialkyl amino group of 1–4 carbon atoms or N-piperidyl or B-morpholinyl, and the other R and $R_1$ are hydrogen, halogen or methoxy and X is a halogen.

14. A method of increasing ionized calcium in a senile male or a post-menopausal or estrogen deficient female patient, comprising administering 12.5 to 100 mg per day of a member selected from the group consisting of clomiphene, an isomer of clomiphene, a citrate of clomiphene, and a derivative of clomiphene to said patient.

15. A method of decreasing the hydroxyproline/creatinine ratio in a male or a post-menopausal or estrogen deficient female patient comprising administering 12.5 to 100 mg per day of a member selected from the group consisting of clomiphene, an isomer of clomiphene, a citrate of clomiphene, and a derivative of clomiphene to said patient.

* * * * *